United States Patent [19]

Wong

[11] Patent Number: 4,639,424
[45] Date of Patent: Jan. 27, 1987

[54] DETERMINATION OF ALKALI METALS

[75] Inventor: Sie-Ting Wong, Mundelein, Ill.

[73] Assignee: Abbott Laboratories, North Chicago, Ill.

[21] Appl. No.: 634,946

[22] Filed: Jul. 27, 1984

Related U.S. Application Data

[63] Continuation-in-part of Ser. No. 544,172, Oct. 21, 1983, abandoned.

[51] Int. Cl.$^4$ .................. G01N 1/18; G01N 21/75; G01N 33/20; G01N 33/50
[52] U.S. Cl. .................................. 436/74; 436/79; 436/164; 436/178
[58] Field of Search ............... 436/74, 79, 164, 171, 436/172, 174, 177, 178, 175

[56] References Cited

PUBLICATIONS

Sumiyoshi et al., *Talanta*, vol. 24, pp. 763–765, 1977.
Jawaid et al., *Talanta*, vol. 25, pp. 91–95, 1978.
Nakamura et al., *Talanta*, vol. 26, pp. 921–927, 1979.
Sanz-Medel et al., *Talanta*, vol. 28, pp. 425–430, 1981.
Takagi et al., *Analytica Chimica Acta*, vol. 126, pp. 185–190, 1981.
Marcus et al., *J. Physical Chemistry*, vol. 82, No. 11, pp. 1246–1254, 1978.
Nakamura et al., *Anal. Chem.*, vol. 52, pp. 1668–1671, 1980.

*Primary Examiner*—Barry S. Richman
*Assistant Examiner*—C. M. Delahunty
*Attorney, Agent, or Firm*—Donald L. Corneglio

[57] ABSTRACT

A method for determining the alkali metal content of a liquid such as protein-containing liquids wherein a liquid containing alkali metal cation is contacted with a monocyclic crown ether capable of forming a complex with the alkali metal cation in a substantially inert solvent and an anionic dye, is disclosed. The alkali metal forms a complex with the ether and the dye in the solvent, the presence of which is a measure of the alkali metal content of the liquid.

2 Claims, No Drawings

DETERMINATION OF ALKALI METALS

REFERENCE TO RELATED APPLICATION

This application is a continuation-in-part of application Ser. No. 544,172, filed Oct. 21, 1983, now abandoned.

BACKGROUND OF THE INVENTION

1. Field of the Invention

This invention relates generally to methods for determining the alkali metal content of liquids, and more specifically to an improved spectrophotometric determination of potassium and sodium cations in protein-containing liquids such as blood serum or plasma.

2. Background Art

Various clinical procedures have evolved over the years for determining alkali metals, notably sodium and potassium, in liquids and particularly in biological fluids such as blood serum. Such procedures are frequently used in monitoring renal functions, as well as being used to detect indications of other diseases. For example, in healthy human beings, the potassium level in the blood serum falls within a narrow range, generally between 3 and 6 millimoles per liter of blood serum. A potassium concentration of only 1.5 millimoles per liter can be fatal, resulting in respiratory depression and cardiac arrhythmia. Because the range of normal potassium level is limited and further because a relatively small deviation from the normal range can be devastating, clinical procedures for determining alkali metal levels must be highly accurate.

Conventional methods for determining the alkali metal content, and specifically sodium and potassium contents, of such fluids as blood serum have been used clinically. Typical of such techniques are flame photometry and ion-specific potentiometry.

One improvement in techniques for determining alkali metals was described by Sumiyoshi and Nakahara in *Talanta*, 24 (1977), 763. In the technique described, potassium was determined photometrically by first forming a complex between potassium and a monocyclic crown ether. The complex was then extracted into benzene as an ion pair with an anionic dye. Thus, the color intensity of the dye was a relatively accurate measure of the potassium content of the solution. Various other similar colorimetric methods have also been described in the literature. See, for example, Takagi, et al., *Analytica Chimica Acta*, 126 (1981), 185. and Charlton, et al., *Clin. Chem.*, 28/9 (1982), 1857.

One of the shortcomings of colorimetric determinations of the prior art, including that disclosed in the aforedescribed Sumiyoshi, et al. article, is that all known methodologies require deproteinization of the serum or plasma being assayed prior to formation of the alkali metal-cryptand complex. The necessity for treatment to remove proteins can affect the alkali metal content of the serum or plasma and thus introduce inaccuracies to the procedure.

SUMMARY OF THE INVENTION

The present invention provides a method for determining the alkali metal content of a liquid which is particularly well suited for use in the analysis of protein-containing biological fluids such as blood serum, plasma, spinal fluid or the like. The method comprises the steps of contacting a liquid containing an alkali metal cation, for example, a sodium or potassium cation, with a monocyclic crown ether capable of forming a complex with the alkali metal cation in the presence of substantially inert, relatively nontoxic organic solvent and an anionic dye. The alkali metal cation present in the liquid is extracted into the solvent and forms a complex with the crown ether which then forms an ion-pair with the anionic dye, preferably at pH levels below 4. Thus, the solvent phase containing the ion-pair is separated, and the color developed by the dye can, for example, be determined spectrophotometrically as a measure of the alkali metal content of the liquid.

It is accordingly an object of the present invention to provide an improved method for the determination of alkali metal ions in liquids, particularly in fluids such as blood serum or plasma, and which does not require prior deproteinization of such fluids.

It is another object of the invention to provide a method for the spectrophotometric determination of alkali metals which is simple, fast and specific to use, and requires a minimum number of reagents.

It is yet another object of the invention to provide a method for the determination of alkali metals in liquids in which substantially inert, relatively low toxicity solvents are employed.

DETAILED DESCRIPTION OF THE INVENTION

In the practice of the present invention, deproteinization of a liquid being assayed prior to formation of the aforementioned complex is not required. Accordingly, the method of the invention can be carried out more rapidly and simply to achieve an accurate analysis of the alkali metal content of the liquid, by comparison with procedures heretofore known.

In the practice of the present invention, use is made, as the cationic complexing agent, of one or more crown ethers capable of forming a complex with an alkali metal such as potassium or sodium. Such monocyclic crown ethers are well known in the art and are macrocyclic polydentate ligands. The monocyclic crown ethers employed in the practice of this invention are preferably the 18-crown-6 and 15-crown-5 monocyclic ethers. Such monocyclic crown ethers are commercially available, for example, from Sigma Chemical Company or Aldrich Chemical Company.

In the present invention, the monocyclic crown ether is preferably used by first dissolving it in a relatively nontoxic, substantially inert organic solvent. By "relatively nontoxic, substantially inert" is meant those organic solvents which are not easily miscible with water, have greater solubility than water for crown ethers and are relatively non-carcinogenic, non-flammable or otherwise substantially known to be not harmful to human health. Solvents suitable for use in the invention include, for example, either halogenated or non-halogenated, substantially inert organic solvents, such as aliphatic or aromatic hydrocarbon solvents, for example preferably selected from the group consisting of carbon tetrachloride, diphenyl ether, 1,2,4-Trichlorobenzene, P-chlorobenzotrifluoride, 3,4-dichlorobenzotrifluoride and trichlorotrifluoroethane, and mixtures thereof. Especially desirable for use in the invention is a halogenated aromatic solvent such as p-chlorobenzotrifluoride, and mixtures thereof with trichlorotrifluoroethane, or a aliphatic solvent such as carbon tetrachloride. The use of such solvents particularly represents an improvement over solvents typically used in the prior art, notably benzene, because of the toxicity of the latter. Moreover, halogenated aliphatic and aromatic solvents, and diphenyl ether, have been found to produce a lower blank, that is, an extract containing less color when no alkali metal is present in the fluid undergoing analysis.

In the practice of the invention, the solution of the monocyclic ether in the solvent is contacted with the liquid under analysis which contains the alkali metal cations, preferably at temperatures lower than about 40 degrees C, and for a time sufficient to reach equilibrium. The alkali metals present in the fluid thus form a complex with the monocyclic crown ether. The complex thus formed between the alkali metal cations and the monocyclic crown ether is then extracted into the solvent as an ion pair with the anionic dye. Accordingly, it is possible to contact the liquid containing the alkali metal cation with the crown ether, the solvent, and the anionic dye, simultaneously. Alternatively, the anionic dye can be added later.

As the anionic dye, use can be made of a variety of anionic dyes which have a measurable color intensity. Preferred for use in the present invention is bromocresol green. Other anionic dyes which are capable of extraction as an ion-pair with the alkali metal-crown ether complex can also be used. The anionic dye is generally used in solution form, preferably with a lower alkanol such as methanol, ethanol, isopropanol and like alcohols containing 1 to 6 carbon atoms serving as the solvent therefor.

The relative proportions of the reagents used in the invention are not critical, and can be varied within broad ranges. For example, it has been found satisfactory to employ a crown ether solution in the organic solvent having a crown ether concentration ranging from about 0.001 to about 1% by weight, depending somewhat on the anticipated concentration of the alkali metal in the solution undergoing analysis. Similarly, the amount of anionic dye dissolved in an alkanol solvent generally has a dye concentration ranging from about 0.005 to about 2.0% by weight.

Having described the basic concepts of the present invention, reference is now made to the following Examples, which are provided by way of illustration, and not by way of limitation, of the present invention.

EXAMPLE 1

Samples of human blood serum were mixed with known aliquots of potassium chloride within the range of from 0 to 30 millimoles (mmoles) of potassium chloride per liter of serum. Forty microliters of each sample were then mixed with 1.5 milliliters (ml) of a 0.3% by weight solution of 18-crown-6 ether in carbon tetrachloride and 1 ml of bromocresol green dissolved in ethanol. (The bromocresol green solution was formed by dissolving 0.075 gram of bromocresol green in 2 ml of ethanol to which 8 ml of lithium acetate (pH 3.8) were added as a stabilizer).

Each of the mixtures was shaken for 15 seconds at room temperature and left to separate into two phases. The carbon tetrachloride phase was separated by centrifugation and then the color intensity, i.e., absorbance, of the carbon tetrachloride solution was measured at 405 nanometers (nm) using a conventional spectrophotometer.

The absorbance of the blank, that is, the carbon tetrachloride extract from a serum sample containing 0 potassium chloride, was 0.408. The absorbance readings measured for each sample were recorded, and the absorbance from the blank subtracted therefrom. The data was then plotted and yielded a linear plot for potassium ion concentrations up to 20 mM. For example, the 5 millimolar (mM) sample of potassium chloride had an absorbance of approximately 0.35, the 10 mM sample had an absorbance of approximately 0.54, and the 20 mM sample had an absorbance of approximately 0.95.

EXAMPLE 2

Samples of human blood serum were mixed with known aliquots of potassium chloride having concentrations ranging from 0–30 millimoles of potassium chloride per liter of serum. Twenty microliters of each sample of serum were then mixed with 3 ml of a 0.0093% by weight solution of 18-crown-6 ether in carbon tetrachloride and 0.5 ml of bromocresol green dissolved in ethanol. (The bromocresol green solution was formed by dissolving 0.2 g of bromocresol green in 2 ml of ethanol, to which 18 ml of 200 mM of lithium acetate (pH 3.8) were added as a stabilizer).

Each of the mixtures was shaken for 15 seconds at room temperature and left to separate into two phases. The carbon tetrachloride phase was separated by centrifugation and then the absorbance of the carbon tetrachloride solution was measured at 405 nm. The absorbance of the blank, that is, the carbon tetrachloride extract from the serum sample containing 0 potassium chloride, was 0.15. The absorbance readings measured for each sample were recorded, and the absorbance from the blank subtracted therefrom. The data, as in Example 1, yielded a linear plot. Thus, the 5 mM sample of potassium chloride had an absorbance of approximately 0.19, the 10 mM sample had an absorbance of approximately 0.38 and the 20 mM sample had an absorbance of approximately 0.76.

EXAMPLE 3

Samples of human blood serum were mixed with known aliquots of potassium chloride within the range of from 0 to 30 millimoles of potassium chloride per liter of serum. Twenty microliters of each sample were mixed with 1.5 ml of a 7.5 mg % by weight solution of 18-crown-6 ether in diphenyl ether (Aldrich Chemical Co.) and 0.45 ml of bromocresol green dissolved in ethanol. (The bromocresol green solution was formed by dissolving 0.20 g of bromocresol green in 0.6 ml of ethanol to which 9.4 ml of 0.2M lithium acetate (pH 3.8) were added as a stabilizer).

Each of the mixtures was shaken for 15 seconds at room temperature and left to separate into two phases. The diphenyl ether phase was separated by centrifugation and absorbance of the diphenyl ether solution was measured at 405 nm.

The absorbance of the blank, that is, the diphenyl ether extract from a serum sample containing 0 potassium chloride was 0.200. The absorbance readings measured for each sample were recorded, and the absorbance from the blank subtracted therefrom. The data was then plotted and yielded a linear plot for potassium ion concentrations up to 20 mM. For example, the 5 mM sample of potassium chloride had an absorbance of approximately 0.44, the 10 mM sample had an absorbance of approximately 0.88, and the 20 mM sample had an absorbance of approximately 1.76.

EXAMPLE 4

Samples of human blood serum were mixed with known aliquots of potassium chloride within the range of from 0 to 30 millimoles of potassium chloride per liter of serum. Twenty microliters of each sample were mixed with 1.5 ml of a 7.5 mg % by weight solution of 18-crown-6 ether in either 1,2,4-Trichlorobenzene (Aldrich Chemical Co.), P-chlorobenzotrifluoride (Sigma Chemical Co.), or 3,4-dichlorobenzotrifluoride (Aldrich Chemical Co.), and 0.45 ml of bromocresol green dissolved in ethanol. (The bromocresol green solution was formed by dissolving 0.20 g of bromocresol green into 0.6 ml of ethanol to which 9.4 ml of 0.2M lithium acetate (pH 3.8) were added as a stabilizer.

Each of the mixtures was shaken for 15 seconds at room temperature and left to separate into two phases. The aromatic solvent phase was separated by centrifugation, and absorbance of the aromatic solvent phase was measured at 405 nm.

The absorbance of the blank, that is, the aromatic solvent extract from a serum sample containing 0 potassium chloride, was 0.07. The absorbance readings measured for each sample were recorded, and the absorbance from the blank subtracted therefrom. The data was then plotted and yielded a linear plot for potassium ion concentrations up to 12 mM and for sodium ion concentrations up to at least 600 mM. For example, the 5 mM sample of potassium chloride had an absorbance of approximately 0.44, the 10 mM sample had an absorbance of approximately 0.88, and the 12 mM sample had an absorbance of approximately 1.25.

EXAMPLE 5

Samples of human blood serum were mixed with known aliquots of potassium chloride within the range of from 0 to 30 millimoles of potassium chloride per liter of serum. Twenty microliters of each sample were mixed with 1.5 ml of a 7.5 mg % by weight solution of 18-crown-6 ether in an organic solvent mixture (The solvent mixture was prepared by mixing 7.5 parts of P-chlorobenzotrifluoride (Sigma Chemical Co.), and 2.5 parts of trichlorotrifluoroethane (Aldrich Chemical Co.) (v/v) and 0.45 ml of bromocresol green dissolved in ethanol. (The bromocresol green solution was formed by dissolving 0.20 g of bromocresol green into 0.6 ml of ethanol, to which 9.4 ml of 0.2M lithium acetate (pH 3.8) was added as a stabilizer).

Each of the mixtures was shaken for 15 seconds at room temperature and left to separate into two phases. The solvent mixture phase was separated by centrifugation, whereafter the color intensity or absorbance of the solvent mixture solution was measured at 405 nm.

The absorbance of the blank, that is, the solvent mixture extract from a serum sample containing 0 potassium chloride, was 0.080. The absorbance readings measured for each sample were recorded, and the absorbance from the blank subtracted therefrom. The data was then plotted and yielded a linear plot for potassium ion concentrations up to 12 mM and for sodium ion concentrations up to at least 600 mM. For example, the 5 mM sample of potassium chloride had an absorbance of approximately 0.44, the 10 mM sample had an absorbance of approximately 0.88, and the 12 mM sample had an absorbance of approximately 1.25.

EXAMPLE 6

Samples of human blood serum were mixed with known aliquots of sodium chloride within the range of from 0 to 400 millimoles of sodium chloride per liter of serum, and the samples analyzed according to the invention substantially as described in Example 1, *supra*, except that the sodium content of the serum was determined rather than potassium, and 15-crown-5 ether was substituted for the 18-crown-6 ether used in the prior Example.

The absorbance of the blank, that is, the carbon tetrachloride extract from a serum containing 0 sodium chloride, was approximately 0.32. The absorbance readings measured for each sample were recorded, and the absorbance of the blank subtracted therefrom. The data was then plotted and yielded a linear plot for sodium ion concentrations up to 400 mM. For example, the 100 mM sample of sodium chloride had an absorbance of approximately 0.11, the 200 mM sample had an absorbance of approximately 0.22, and the 400 mM sample had an absorbance of approximately 0.44.

While the invention has been described in relation to the use of a colored anionic dye, it will be understood by those skilled in the art that many other types of dyes can also be used, for example, fluorescent dyes and chemiluminescent dyes, which can be detected by means well known to those skilled in the art. For example, fluorescent dyes can be detected using a fluorimeter.

It will be understood that various changes and modifications can be made in the details, procedure, formulation and use of the invention as described herein without departing from the spirit and scope thereof, as defined solely in the claims appended hereto. For example, although the practice of the invention has been described in connection with the assay of potassium and sodium ions in blood serum or plasma, it will be appreciated that these as well as other alkali metals can be similarly assayed, in a wide variety of liquids, such as water, industrial fluids and the like, utilizing the principles of the invention. In addition, it is to be appreciated that the invention is not limited to the reagents and solvents specified and described herein, but that many other suitable substitutes for those specified will become apparent to those skilled in the art, given the teachings hereof.

What is claimed is:

1. A method for determining the alkali metal content of a protein-containing liquid which has not been treated to remove proteins, which method comprises the steps of:
    (a) contacting the protein-containing liquid containing an alkali metal cation with (1) a monocyclic crown ether capable of forming a complex with the alkali metal cation, (2) a solvent selected from the group consisting of diphenyl ether, p-chlorobenzotrifluoride, 3,4-dichlorobenzotrifluoride, 1,2,4-trichlorobenzene, trichlorotrifluoroethane and mixtures thereof, and (3) an anionic dye to form a reaction mixture having an aqueous phase and a phase containing said solvent;
    (b) separating from the mixture of step (a) the solvent phase, said phase containing said solvent containing a complex of the alkali metal cation, the crown ether and the anionic dye; and
    (c) determining the concentration of the dye in the solvent phase as a measure of the alkali metal content of the protein-containing liquid.

2. A method as defined in claim 1, wherein the protein-containing liquid is a blood serum.

* * * * *